United States Patent
Rozenberg et al.

(10) Patent No.: US 10,076,441 B2
(45) Date of Patent: Sep. 18, 2018

(54) DEVICES FOR COOLING THE NASAL CAVITY

(71) Applicant: BrainCool AB, Lund (SE)

(72) Inventors: Allan Rozenberg, San Diego, CA (US); John K Hoffman, Poway, CA (US); James D Savage, San Diego, CA (US)

(73) Assignee: BrainCool AB, Lund (SE)

( * ) Notice: Subject to any disclaimer, the term of this patent is extended or adjusted under 35 U.S.C. 154(b) by 73 days.

(21) Appl. No.: 15/174,737

(22) Filed: Jun. 6, 2016

(65) Prior Publication Data

US 2017/0027746 A1 Feb. 2, 2017

Related U.S. Application Data

(60) Continuation of application No. 13/963,238, filed on Aug. 9, 2013, now abandoned, which is a
(Continued)

(51) Int. Cl.
*A61F 7/12* (2006.01)
*A61M 3/02* (2006.01)
(Continued)

(52) U.S. Cl.
CPC ............... *A61F 7/123* (2013.01); *A61F 7/12* (2013.01); *A61M 3/025* (2013.01);
(Continued)

(58) Field of Classification Search
CPC ...... A61F 2007/0006; A61F 2007/0068; A61F 2007/0214; A61F 2007/0247; A61F 7/12;
(Continued)

(56) References Cited

U.S. PATENT DOCUMENTS 3,516,407 A 6/1970 Ruggero
3,766,924 A 10/1973 Pidgeon
(Continued)

FOREIGN PATENT DOCUMENTS

DE 19952440 5/2001
EP 0692273 A1 1/1996
(Continued)

OTHER PUBLICATIONS

Bluestone et al., "Intranasal Freezing for Severe Epistaxis," *International Surgery* Jan. 1970; 53(1):11-15.
(Continued)

*Primary Examiner* — Quynh-Nhu H Vu
(74) *Attorney, Agent, or Firm* — Capitol City TechLaw

(57) ABSTRACT

A method for cerebral cooling is described using a cooling assembly, which includes first and second elongate tubular members adapted for insertion into a nasal cavity of a patient through the patient's nostrils. The elongate tubular members each have a proximal end, a distal end, a lumen extending therebetween, and a plurality of ports in fluid communication with the lumen. The cooling assembly also includes a manifold and a reservoir, which contains a pressurized fluid that includes a propellant having a boiling point less than 22° C. The elongate tubular members are inserted into the nasal cavity through the patient's nostrils and pressurized fluid is delivered onto a surface of the nasal cavity by infusing the pressurized fluid from the reservoir through the manifold, into the lumens and through the plurality of ports of the first and second elongate tubular members.

4 Claims, 8 Drawing Sheets

Related U.S. Application Data continuation of application No. 13/439,772, filed on Apr. 4, 2012, now Pat. No. 8,512,280, which is a division of application No. 12/819,116, filed on Jun. 18, 2010, now Pat. No. 8,157,767.

(60) Provisional application No. 61/218,774, filed on Jun. 19, 2009.

(51) Int. Cl.
    *A61M 13/00* (2006.01)
    *A61M 16/20* (2006.01)
    *A61M 25/10* (2013.01)
    *A61M 16/04* (2006.01)
    *A61F 7/00* (2006.01)
    *A61F 7/02* (2006.01)

(52) U.S. Cl.
    CPC ........ *A61M 3/0295* (2013.01); *A61M 13/003* (2013.01); *A61M 16/045* (2014.02); *A61M 16/0409* (2014.02); *A61M 16/0461* (2013.01); *A61M 16/208* (2013.01); *A61M 16/209* (2014.02); *A61M 25/10* (2013.01); *A61F 2007/0006* (2013.01); *A61F 2007/0068* (2013.01); *A61F 2007/0214* (2013.01); *A61F 2007/0247* (2013.01); *A61M 2025/1052* (2013.01); *A61M 2205/3606* (2013.01); *A61M 2210/0618* (2013.01)

(58) Field of Classification Search
    CPC . A61F 7/123; A61M 13/003; A61M 16/0409; A61M 16/045; A61M 16/208; A61M 16/209; A61M 2025/1052; A61M 2205/3606; A61M 2210/0618; A61M 25/10; A61M 3/025; A61M 3/0295
    See application file for complete search history.

(56) References Cited

U.S. PATENT DOCUMENTS

| | | |
|---|---|---|
| 4,095,593 A | 6/1978 | Webbon |
| 4,138,743 A | 2/1979 | Elkins |
| 4,819,619 A | 4/1989 | Augustine et al. |
| 4,821,715 A | 4/1989 | Downing |
| 4,895,562 A | 1/1990 | Lopez |
| 5,158,536 A | 10/1992 | Sekins et al. |
| 5,346,471 A | 9/1994 | Raulerson |
| D354,376 S | 1/1995 | Kun |
| 5,460,610 A | 10/1995 | Don Michael |
| 5,540,225 A | 7/1996 | Schutt |
| 5,568,884 A | 10/1996 | Bruna |
| 5,624,392 A | 4/1997 | Saab |
| 5,702,362 A | 12/1997 | Herold et al. |
| 5,746,717 A | 5/1998 | Aigner |
| 5,792,100 A | 8/1998 | Shantha |
| 5,836,967 A | 11/1998 | Schneider |
| 5,899,878 A | 5/1999 | Glassman |
| 5,908,407 A | 6/1999 | Frazee et al. |
| 5,927,273 A | 7/1999 | Federowicz |
| RE36,460 E | 12/1999 | Klatz |
| 6,027,478 A | 2/2000 | Katz |
| 6,030,412 A | 2/2000 | Klatz |
| 6,090,132 A | 7/2000 | Fox |
| 6,149,624 A | 11/2000 | McShane |
| 6,156,057 A | 12/2000 | Fox |
| 6,166,092 A | 12/2000 | Sekins |
| 6,178,562 B1 | 1/2001 | Elkins |
| 6,303,156 B1 | 10/2001 | Ferrigno |
| 6,352,550 B1 | 3/2002 | Gildersleeve |
| 6,386,202 B1 | 5/2002 | Frazee |
| 6,398,774 B1 | 6/2002 | Penner et al. |
| 6,537,246 B1 | 3/2003 | Unger et al. |
| 6,548,049 B1 | 4/2003 | Cutie et al. |
| 6,647,930 B2 | 11/2003 | Nurmi |
| 6,682,499 B2 | 1/2004 | Lenker |
| 6,695,872 B2 | 2/2004 | Elkins |
| 6,730,115 B1 | 5/2004 | Heaton |
| 6,736,837 B2 | 5/2004 | Fox |
| 6,749,597 B2 | 6/2004 | Frank |
| 6,796,972 B1 | 9/2004 | Sinofsky et al. |
| 6,929,003 B2 | 8/2005 | Blacker |
| 6,959,708 B1 | 11/2005 | Rasor et al. |
| 6,983,749 B2 | 1/2006 | Kumar |
| 7,077,825 B1 | 7/2006 | Stull |
| 7,189,253 B2 | 3/2007 | Lunderqvist et al. |
| 7,204,822 B1 | 3/2007 | Lunderqvist et al. |
| 7,686,781 B2 | 3/2010 | Vinten-Johansen |
| 7,824,436 B2 | 11/2010 | Barbut |
| 8,157,767 B2 | 4/2012 | Rozenberg et al. |
| 8,512,280 B2 | 8/2013 | Rozenberg et al. |
| 2001/0008652 A1 | 7/2001 | Hamada et al. |
| 2001/0016764 A1 | 8/2001 | Dokab |
| 2002/0023640 A1 | 2/2002 | Nightengale |
| 2002/0045924 A1 | 4/2002 | Fox |
| 2002/0055746 A1 | 5/2002 | Burke et al. |
| 2002/0077593 A1 | 6/2002 | Perkins |
| 2002/0091426 A1 | 7/2002 | Fox |
| 2002/0138121 A1 | 9/2002 | Fox |
| 2002/0161349 A1 | 10/2002 | Allers |
| 2003/0131844 A1 | 7/2003 | Kumar |
| 2003/0181416 A1 | 9/2003 | Comper |
| 2004/0049154 A1 | 3/2004 | Larnard |
| 2004/0127813 A1 | 7/2004 | Schwamm |
| 2004/0167594 A1 | 8/2004 | Elkins |
| 2004/0210236 A1 | 10/2004 | Allers |
| 2004/0215163 A1 | 10/2004 | Walker |
| 2005/0065469 A1 | 3/2005 | Tal |
| 2005/0113799 A1 | 5/2005 | Lenker |
| 2005/0152844 A1 | 7/2005 | Barbut et al. |
| 2005/0154430 A1 | 7/2005 | Barbut et al. |
| 2005/0159703 A1 | 7/2005 | Yokoyama et al. |
| 2005/0209662 A1 | 9/2005 | Lunderqvist |
| 2006/0052854 A1 | 3/2006 | Allers |
| 2006/0276552 A1* | 12/2006 | Barbut ............ A61F 7/12 514/743 |
| 2007/0050002 A1 | 3/2007 | Elfteriades |
| 2007/0123813 A1 | 5/2007 | Barbut |
| 2007/0129665 A1 | 6/2007 | Dickens et al. |
| 2008/0004613 A1 | 1/2008 | Barbut |
| 2008/0086186 A1 | 4/2008 | Takeda et al. |
| 2008/0114286 A1 | 5/2008 | Hamel et al. |
| 2008/0215002 A1 | 9/2008 | Rozenberg |
| 2008/0249188 A1 | 10/2008 | Barbut |
| 2009/0107491 A1 | 4/2009 | Belson |
| 2009/0165786 A1 | 7/2009 | Barbut |
| 2009/0234325 A1 | 9/2009 | Rozenberg |
| 2010/0174278 A1 | 7/2010 | Barbut |
| 2010/0211140 A1 | 8/2010 | Barbut |

FOREIGN PATENT DOCUMENTS

| | | |
|---|---|---|
| EP | 1888156 | 2/2008 |
| JP | 2005287548 A | 10/2005 |
| WO | WO 98/23217 | 6/1998 |
| WO | WO 01/93922 | 12/2001 |
| WO | WO 03/066137 | 8/2003 |
| WO | WO 2005/070144 | 8/2005 |
| WO | WO 2005/087156 | 9/2005 |
| WO | WO 2006/124702 | 11/2006 |
| WO | WO 2008/063179 | 5/2008 |
| WO | WO 2008/094509 | 8/2008 |
| WO | WO 2010/054249 | 5/2010 |

OTHER PUBLICATIONS

Brain, "Cryosurgery in Benign Condition of the Nose and Throat," *Proc. Roy. Soc. Med.* Jan. 1974; 67(1):72-76.

Hagioka et al., "Nasopharyngeal Cooling Selectively and Rapidly Decreases Brain Temperature and Attenuates Neuronal Damage,

(56) References Cited

OTHER PUBLICATIONS

Even If Initiated at the Onset of Cardiopulmonary Resuscitation in Rats," *Crit Care Med* 003, vol. 31, No. 10, pp. 2502-2508 (2003).
Harris et al., "Rapid (0.5"C/min) minimally invasive induction of hypothermia using cold perfluorochemical lung lavage in dogs," *Resuscitation* 50 (2001), pp. 189-204.
Maloney et al., "Selective Brain Cooling: Role of Angularis Oculi Vein and Nasal Thermoreception," *Am. J. Physiol. Regul. Comp. Physiol.* 273:1108-1116 (1997).
Mariak et al., "Direct Cooling of the Human Brain by Heat Loss From the Upper Respiratory Tract," *J. App. Physiol.* 87(5): 1609-1613 (1999).
Mellergard, "Changes in Human Intracerebral Temperature in Response to Difference Methods of Brain Cooling," *Neurosurgery*, vol. 31, No. 4, Oct. 1992.
Natale et al., "Protection From Cerebral Ischemia by Brain Cooling Without Reduced Lactate Accumulation in Dogs," *Stroke*, vol. 20, No. 6, Jun. 1989, pp. 770-777.

\* cited by examiner

DEVICES FOR COOLING THE NASAL CAVITY

This application is a continuation of U.S. application Ser. No. 13/963,238, filed Aug. 9, 2013, which is a continuation of U.S. Ser. No. 13/439,772, entitled "Devices for Cooling the Nasal Cavity," filed Apr. 4, 2012, now U.S. Pat. No. 8,512,280, which is a divisional of U.S. Ser. No. 12/819,116, entitled "Devices for Cooling the Nasal Cavity," filed on Jun. 18, 2010, now U.S. Pat. No. 8,157,767, which claims the benefit of U.S. provisional patent application Ser. No. 61/218,774, entitled "Device for Cooling the Nasal Cavity," filed Jun. 19, 2009, all of which are expressly incorporated herein by reference in their entirety for all purposes.

FIELD OF THE INVENTION

The invention relates to cerebral and systemic cooling via the nasal cavity, oral cavity, and other parts of the body, and more particularly to methods and devices for cerebral and systemic cooling using liquids or liquid mists and for delivering liquid mists to the nasopharyngeal cavity.

BACKGROUND OF THE INVENTION

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. Within minutes of circulatory failure, tissues become ischemic, particularly in the heart and brain.

The most common form of shock is cardiogenic shock, which results from severe depression of cardiac performance. The most frequent cause of cardiogenic shock is myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, acutely acquired ventricular septal defects, can also cause cardiogenic shock by reducing cardiac output. Additional causes of cardiogenic shock include cardiac arrhythmia, such as ventricular fibrillation. With sudden cessation of blood flow to the brain, complete loss of consciousness is a sine qua non in cardiac arrest. Cardiac arrest often progresses to death within minutes if active interventions, e.g., cardiopulmonary resuscitation (CPR), defibrillation, use of inotropic agents and vasoconstrictors such as dopamine, dobutamine, or epinephrine, are not undertaken promptly. The most common cause of death during hospitalization after resuscitated cardiac arrests is related to the severity of ischemic injury to the central nervous system, e.g., anoxic encephalopathy. The ability to resuscitate patients of cardiac arrest is related to the time from onset to institution of resuscitative efforts, the mechanism, and the clinical status of the patient prior to the arrest.

Focal cerebral ischemia refers to cessation or reduction of blood flow within the cerebral vasculature resulting in stroke, a syndrome characterized by the acute onset of a neurological deficit that persists for at least 24 hours, reflecting focal involvement of the central nervous system. Approximately 80% of the stroke population is hemispheric ischemic strokes, caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. Hemorrhagic stroke accounts for the remaining 20% of the annual stroke population. Hemorrhagic stroke often occurs due to rupture of an aneurysm or arteriovenous malformation bleeding into the brain tissue, resulting in cerebral infarction. Other causes of focal cerebral ischemia include vasospasm due to subarachnoid hemorrhage from head trauma or iatrogenic intervention.

Current treatment for acute stroke and head injury is mainly supportive. A thrombolytic agent, e.g., tissue plasminogen activator (t-PA), can be administered to non-hemorrhagic stroke patients. Treatment with systemic t-PA is associated with increased risk of intracerebral hemorrhage and other hemorrhagic complications. Aside from the administration of thrombolytic agents and heparin, there are no therapeutic options currently on the market for patients suffering from occlusion focal cerebral ischemia. Vasospasm may be partially responsive to vasodilating agents. The newly developing field of neurovascular surgery, which involves placing minimally invasive devices within the carotid arteries to physically remove the offending lesion, may provide a therapeutic option for these patients in the future, although this kind of manipulation may lead to vasospasm itself.

In both stroke and cardiogenic shock, patients develop neurological deficits due to reduction in cerebral blood flow. Thus treatments should include measures to maintain viability of neural tissue, thereby increasing the length of time available for interventional treatment and minimizing brain damage while waiting for resolution of the ischemia. New devices and methods are thus needed to minimize neurologic deficits in treating patients with either stroke or cardiogenic shock caused by reduced cerebral perfusion.

Research has shown that cooling the brain may prevent the damage caused by reduced cerebral perfusion. Initially research focused on selective cerebral cooling via external cooling methods. Studies have also been performed that suggest that the cooling of the upper airway can directly influence human brain temperature, see for example *Direct cooling of the human brain by heat loss from the upper respiratory tract*, Zenon Mariak, et al. 8750-7587 *The American Physiological Society* 1999, incorporated by reference herein in its entirety. Furthermore, because the distance between the roof of the nose and the floor of the anterior cranial fossa is usually only a fraction of a millimeter, the nasal cavity might be a site where respiratory evaporative heat loss or convection can significantly affect adjacent brain temperatures, especially because most of the warming of inhaled air occurs in the uppermost segment of the airways. Thus, it would be advantageous to develop a device and method for achieving cerebral cooling via the nasal and/or oral cavities of a patient.

SUMMARY OF THE INVENTION

The invention relates to methods and devices for providing cerebral and systemic cooling via the nasal cavity. The cooling occurs by direct heat transfer through the nasal cavity and/or nasopharynx as well as by hematogenous cooling through the carotids as they pass by the oropharynx and through the Circle of Willis, which lies millimeters away from the pharynx. The direct cooling will be obtained through evaporative heat loss of a nebulized liquid in the nasal cavity. Additionally, cooling may occur through convection in the nasal cavity. Such cerebral cooling may help to minimize neurologic deficits in treating patients with either stroke or cardiogenic shock caused by reduced cerebral perfusion or in the treatment of migraines. In the following description, where a cooling assembly, device, or method is described for insertion into a nostril of a patient, a second cooling assembly or device can optionally also be inserted into the other nostril to maximize cooling.

In one embodiment, the invention provides a method for cerebral cooling via the nasal cavity using a self-contained cooling and delivery system. A cooling assembly including an elongate tubular member having a proximal end, a distal end, a first lumen extending therebetween, a plurality of ports in fluid communication with the first lumen and a second lumen extending between proximal and distal ends, the second lumen communicating with a balloon mounted on the first elongate tubular member distal the plurality of ports is provided. The cooling assembly also includes a manifold in fluid communication with the first and second lumens of the elongate tubular member and further communicating with a second elongate tubular member which is also in fluid communication with a reservoir containing a pressurized fluid via the second elongate tubular member. The elongate tubular member is inserted into a nasal cavity of a patient through the patient's nostril such that the balloon and plurality of ports are positioned in the nasal cavity. The balloon is inflated by infusing fluid and/or pressure from the reservoir through the manifold and into the second lumen. The pressurized fluid is then delivered onto a surface of the patient's nasal cavity by infusing the pressurized fluid from the reservoir through the manifold into the first lumen and through the plurality of ports. The fluid preferably comprises a refrigerant having a boiling point of 37° Celsius or below such that it will evaporate upon contact with the nasal cavity surface. The evaporation of the fluid from the nasal cavity preferably results in reduction of the cerebral temperature of the patient by at least 0.5° C. in one hour. Alternatively, the cerebral temperature may be reduced by at least 1.0° C. in one hour, alternatively at least 1.5° C. in one hour, alternatively at least 2° C. in one hour, alternatively at least 2.5° C. in one hour, alternatively at least 3° C. in one hour, alternatively at least 4° C. in one hour, alternatively at least 5° C. in one hour, alternatively at least 6° C. in one hour, alternatively at least 7° C. in one hour. A pressure release valve in the manifold may be activated to deflate the balloon at the completion of the delivery of fluid to the nasal cavity. Alternatively, if additional cooling is desired, a second pressurized fluid container may be connected to the manifold to continue treatment.

In another embodiment, the invention provides a self-contained cooling assembly including a pressurized fluid source that is capable of delivering a cooling fluid that evaporates in to a patient's nasal cavity and automatically inflating an occluding balloon located on the distal end of the cooling assembly using pressure from the pressurized fluid source. The cooling assembly includes a first elongate tubular member adapted for insertion into the nasal cavity of a patient, a manifold and a reservoir containing a pressurized fluid. The first elongate tubular member has proximal and distal ends, first and second lumens extending therebetween, a plurality of ports located in the distal region in fluid communication with the first lumen, and a balloon mounted on the elongate tubular member distal the plurality of ports in fluid communication with the second lumen. The manifold is in fluid communication with the first and second lumens of the elongate tubular member and a second tubular member which is in fluid communication with the reservoir such that pressurized fluid passes from the reservoir, through the manifold, and into the second lumen to inflate the balloon and into the first lumen and through the plurality of ports.

In use, the elongate member is inserted into a nasal cavity of a patient through one of the patient's nostrils and positioned in the nasal cavity. The elongate member may be positioned in the nasal cavity such that the balloon on the distal end of the elongate member will contact the walls of the posterior nasal cavity and form a seal between the nasal cavity and the patient's nasopharynx when inflated. Alternatively, the elongate tubular member may be positioned such that the balloon will contact the nasopharynx and form a seal between the nasal cavity and the patient's nasopharynx when inflated. The ports on the distal region of the elongate member will then be positioned to deliver a nebulized liquid spray over the surface of the nasal cavity, including the nasal plexus and the carotids. The proximal end of the elongate member is placed in fluid communication with a pressurized fluid source via a manifold. Pressure from the pressurized fluid source is used to push liquid and/or vapor from the pressurized fluid source into the elongate tubular member. The manifold controls delivery of the fluid to the elongate member such that liquid and/or vapor is first delivered through a lumen in fluid communication with the balloon mounted on the distal end of the elongate member to inflate the balloon. Once the balloon has been inflated, a check valve in the manifold opens and allows the fluid, including both liquid and vapor, to be delivered though a second lumen in fluid communication with the ports located on the distal region of the elongate member. A liquid spray is delivered into the patient's nasal cavity through the plurality of ports. In one embodiment, the liquid is nebulized at each of the plurality of ports on the elongate member. The fluid has a boiling point equal to or less than 37° Celsius such that a majority of the fluid will be delivered in liquid form and will evaporate upon contact with the surface of the nasal cavity. Some of the fluid though will evaporate during transit and become vapor. Cooling will be both from the vapor, which is chilled from the evaporation that created it, and also from the liquid spray as it evaporates in the nasal cavity. The volume of liquid delivered from a single pressurized canister may be range from about 0.05 to about 1 Liter. For example, it is envisioned that a single pressurized canister could deliver about 50 mL of cooling liquid, alternatively about 100 mL, alternatively about 200 mL, alternatively about 0.5 Liters, alternatively about 0.75 Liters, alternatively about 1 Liter of cooling liquid. Depending on the cooling fluid used, these volumes of cooling fluid may provide cooling for approximately 10 minutes, alternatively up to 30 minutes, alternatively up to one hour. In addition, it is further envisioned that additional cooling time may be provided, if needed, by attaching additional canisters to the cooling assembly. The inflated balloon prevents unevaporated fluid from being inhaled by the patient. In some embodiments, the unevaporated fluid may also be suctioned or otherwise removed from the patient's nasal cavity via a suction lumen in the elongate tubular member.

DETAILED DESCRIPTION

Figure 1:
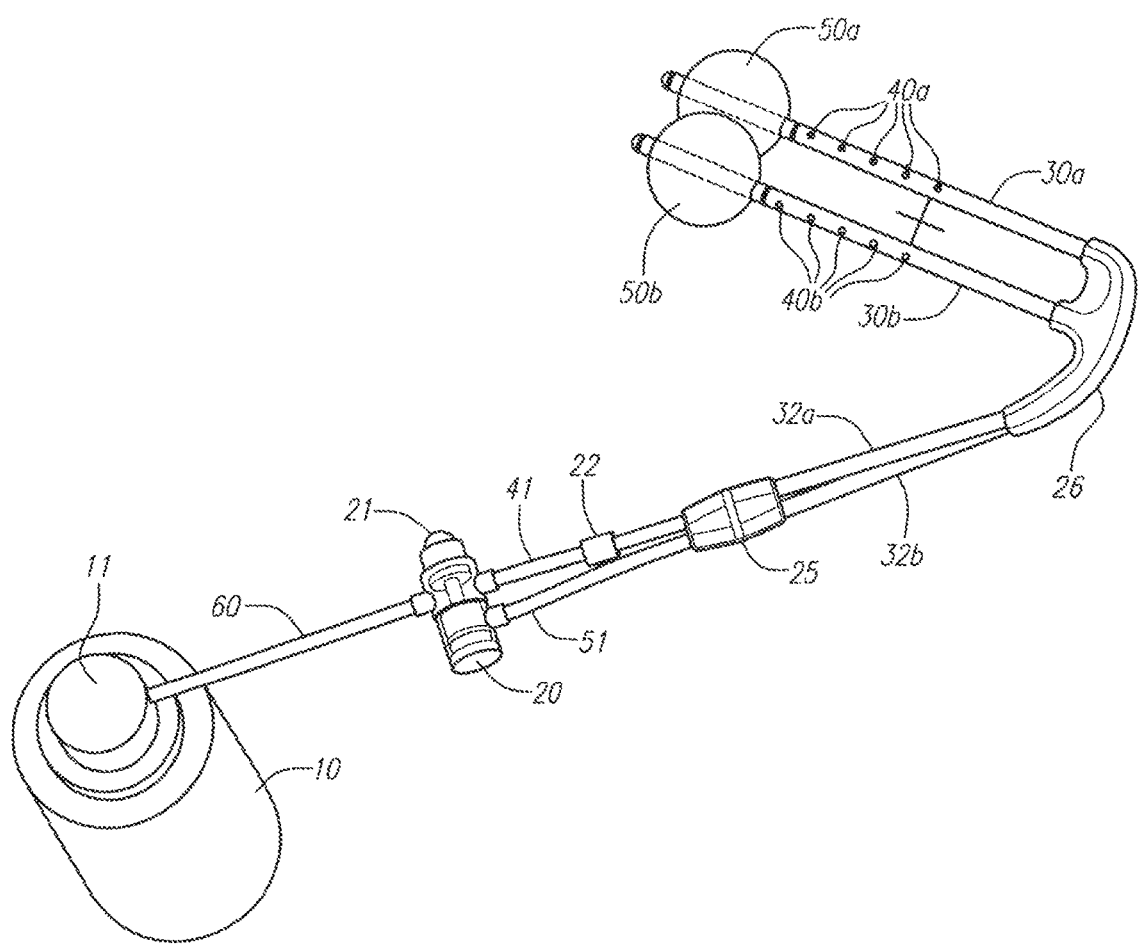
FIG. 1 illustrates an embodiment of a device having a pressurized source for delivering a fluid to the nasal cavity according to the present invention for non-invasive cerebral and systemic cooling.

Described herein are devices and methods for delivering, from a pressurized source, a fluid that evaporates in the nasal cavity to provide cerebral and or systemic cooling. The approach is a self contained methodology which is designed for emergent care at the site of the injury. Essentially, this process provides a device and method for rapidly administering therapeutic hypothermia in an out-of-hospital setting, such as by emergency or ambulance personnel by developing an endothermic reaction within the nasal pharyngeal space, a mini-internal refrigeration unit. This approach eliminates the need for external refrigeration units, and large ventilation units which are not portable.

The device includes at least one nasal catheter in fluid communication with a pressurized fluid source for delivering a liquid spray of the fluid, which has a boiling point equal to or less than body temperature. In some embodiments, the device includes two nasal catheters such that one nasal catheter is positions within each of a patient's nostrils to maximize cooling. The device also has a balloon(s) on the distal end of the nasal catheter(s) that is inflated from some of the pressure from the pressurized source. In this device, the balloon(s) is inflated and the fluid is delivered to the nasal cavity using the pressure from the pressurized fluid source without the use of pumps or electronics. By using a pressure from the pressurized fluid source to inflate the balloon and deliver the fluid to the nasal cavity, the approach further improves the ease of use and portability of the cooling assembly.

The purpose for the fluid is to cool the nasal cavity, which in turn cools the brain. The purpose for the balloon(s) is to keep most, if not all, un-evaporated fluids or gases from being inhaled or swallowed by the patient. The cooling fluid may be any refrigerant having a boiling point of 37° Celsius or less. Fluids having a boiling point at or below body temperature, i.e., 37° Celsius, will evaporate upon contact with the walls of the nasal cavity without the need to deliver an additional gas to enhance evaporation. For example, the cooling fluid may be, but is not limited to, a perfluorocarbon, a fluorocarbon, a hydrofluorocarbon, or any mixture thereof, having a boiling point of approximately 37° Celsius or less. In some embodiments, a propellant having a boiling point at or below room temperature, i.e., approximately 22° Celsius, may be used to pressurize the fluid reservoir in order to deliver the cooling fluid to inflate the balloon and cool the nasal cavity. The propellant may also be, but is not limited to, a perfluorocarbon, a fluorocarbon, a hydrofluorocarbon, having a boiling point at or below approximately 22° Celsius. The propellant may be mixed in with the fluid in the fluid reservoir or alternatively, the fluid and propellant may remain separated in the pressurized fluid reservoir. For example, the cooling fluid may be provided in a separate bladder surrounded by the propellant, as known in the art, to prevent mixing of the propellant and cooling fluid. Alternatively, the cooling fluid may have a boiling point at or below approximately 22° Celsius, such that the cooling fluid can function as the propellant as well.

The patient's cerebral, systemic and/or nasal temperatures may be monitored during this process. The liquid spray may be delivered at a rate sufficient to achieve a gradient of not more than 0.5° Celsius between the outer surface of the brain and the inner core of the brain. The liquid spray may also be delivered at a flow rate sufficient to achieve a gradient of at least about 1.0° Celsius between the cerebral temperature and systemic temperature. The liquid spray may also be delivered at a flow rate sufficient to achieve cerebral cooling at a rate greater that about 1.0° Celsius in one hour. The liquid spray may also be delivered at a flow rate sufficient to achieve a temperature in the nasal cavity of about 4.0° Celsius. In some embodiments, the liquid spray may be nebulized at each of the plurality of ports just prior to being delivered to the nasal cavity.

Figure 2:
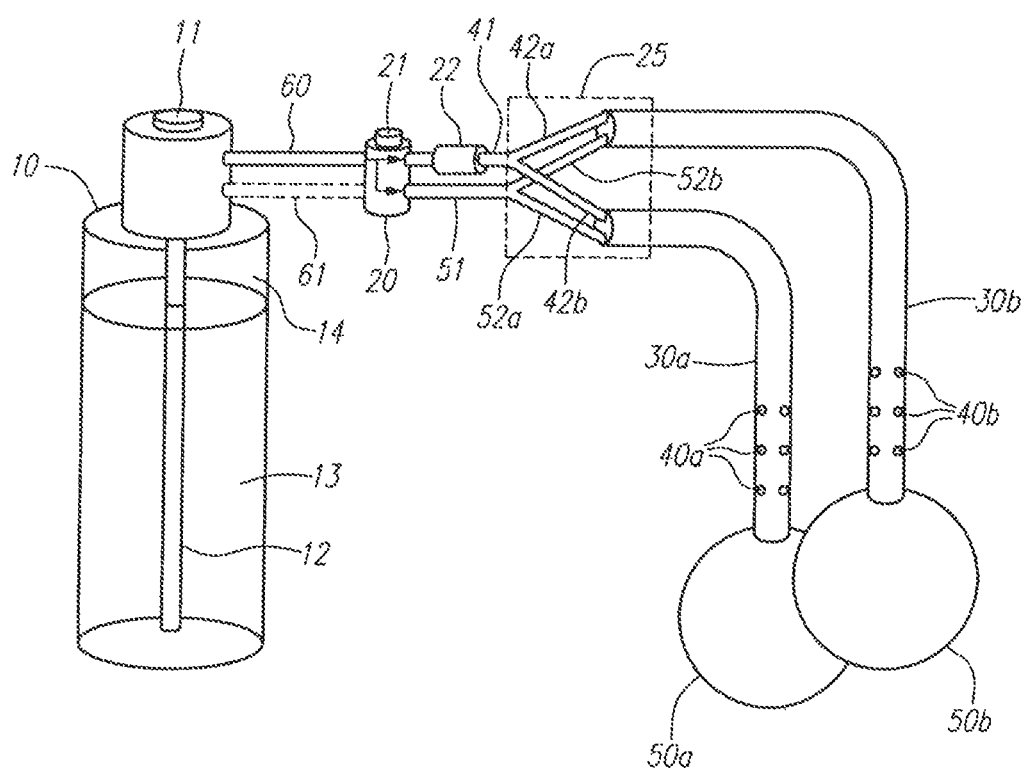
FIG. 2 illustrates an embodiment or a device having a pressurized source for delivering a fluid to the nasal cavity according to the present invention for non-invasive cerebral and systemic cooling.
Figure 3:
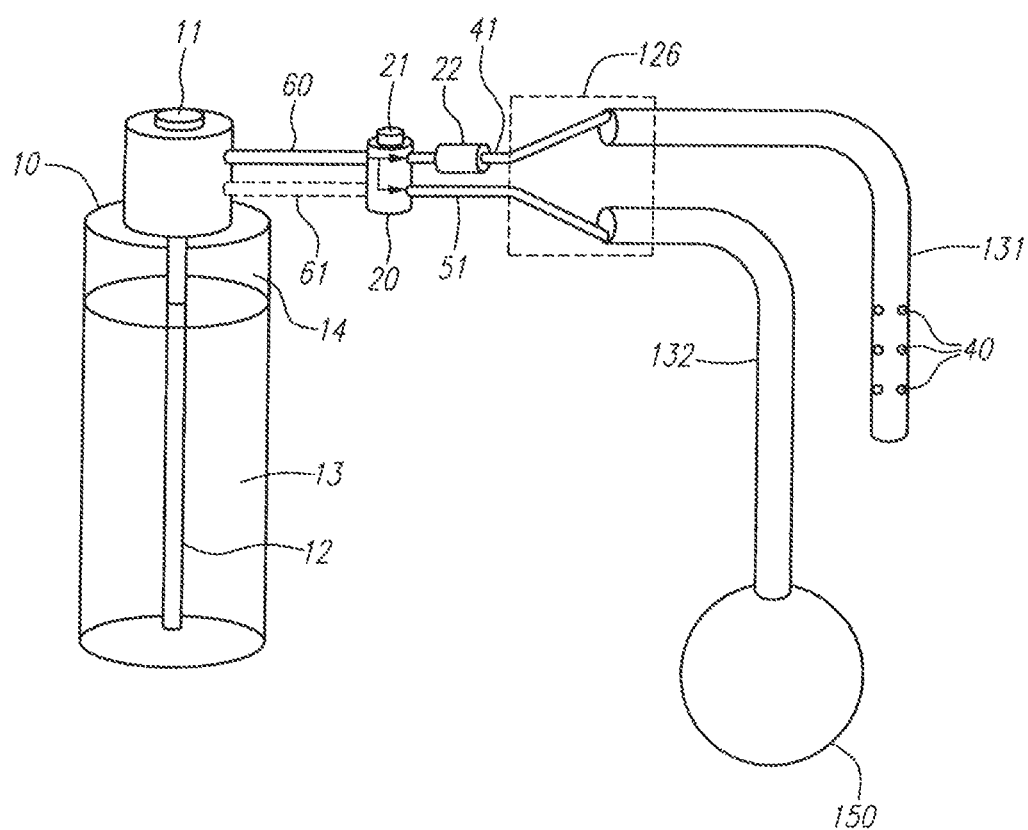
FIG. 3 illustrates an alternative embodiment of a device having a pressurized source for delivering a fluid to the nasal cavity according to the present invention for non-invasive cerebral and systemic cooling.

FIGS. 1-2 illustrate an embodiment of a self-contained system for delivering a fluid to the nasal cavity of a patient for providing cerebral and or systemic cooling. The cooling system includes a pressurized fluid source, a delivery assembly, and a cooling assembly. The pressurized fluid source includes a pressurized container 10 filled with a fluid 13 to be delivered to the nasal cavity and, optionally, a separate propellant. The container 10 may be an aerosol type container or any general pressure container, as known in the art. In some embodiments, the container 10 includes a propellant 14 having a boiling point less than room temperature for pressurizing the container and delivering the fluid 13. Alternatively, the boiling point of the fluid 13 may be at or below room temperature such that evaporation of some of the fluid itself may be used to pressurize the container and deliver the fluid. When a separate propellant is provided, the propellant and fluid are provided in a ratio sufficient to ensure that all the fluid is pushed out of the container.

The container body is of a hollow, cylindrical shape and constructed of a material able to withstand the pressure from the contents. The container is preferably sized to provide a volume of cooling fluid ranging from about 0.05 Liters to about 1 Liter. For example, it is envisioned that a single pressurized container could deliver about 50 mL of cooling liquid, alternatively about 100 mL, alternatively about 200 mL, alternatively about 0.5 Liters, alternatively about 0.75 Liters, alternatively about 1 Liter of cooling liquid. Depending on the cooling fluid used, these volumes of cooling fluid may provide cooling for approximately 10 minutes, alternatively up to 30 minutes, alternatively up to one hour. Moreover, in some embodiments, more than one container may be used to provide additional cooling time.

The top of container 10 has a cap 11 which includes a valve, such as a push-down valve stem, that is in fluid communication with a dip tube 13 extending to the bottom of the container 10. The cap 11 also has an outlet channel in fluid communication with the valve assembly. The outlet channel is in fluid communication with a tubular member 60 connecting the pressurized fluid source 10 to the cooling assembly. The cap 11 may be depressed, turned, or otherwise actuated to open the valve connecting the dip tube 12 and tubular member 60. Opening the valve will allow the pressure from the propellant, or fluid vapor, 14 to force the fluid 13 through the dip tube 12 and into the tubular member 60 for delivery to the cooling assembly. In some embodiments, depressing or turning the cap may lock the valve into an open position. The cap 11 may be pressed again or turned back to close the valve, for example, to stop delivery of the fluid to tubular member 60 in the event that cooling needs to be interrupted or terminated. In some embodiments, the cap 11 may also contain a fluid flow controlling device, such as a needle type valve or a variable diameter aperture to adjust the flow rate of fluid into tubular member 60. Here, the cap 11 may include a selector which would allow the operator to choose one of several choices for the flow rate, for example, low flow, medium flow, high flow.

Figure 4A:
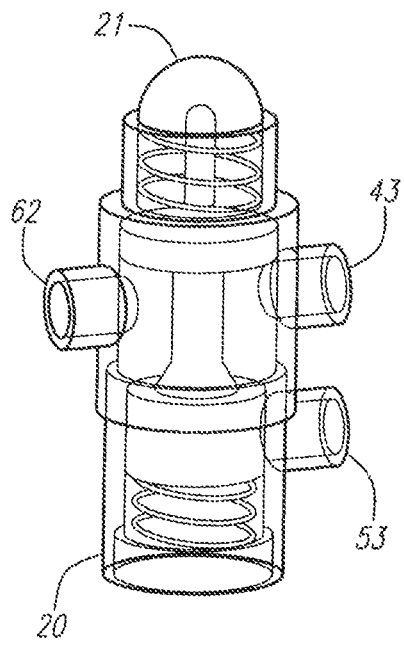
FIG. 4A illustrates an embodiment of a manifold for use with a device having a pressurized source for delivering a fluid to the nasal cavity according to the present invention for non-invasive cerebral and systemic cooling.
Figure 4B:
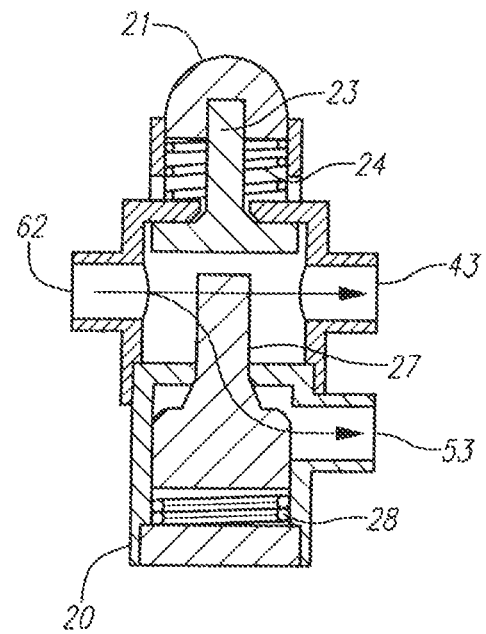
FIG. 4B illustrates a check valve in the manifold of FIG. 3B allowing pressure to move distally when the manifold is pressurized.
Figure 4C:
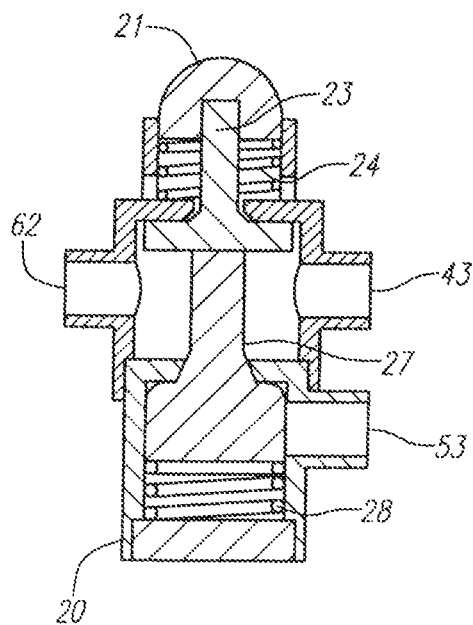
FIG. 4C illustrates a check valve in the manifold of FIG. 3B preventing pressurized fluid from flowing proximally when the manifold is not pressurized.
Figure 4D:
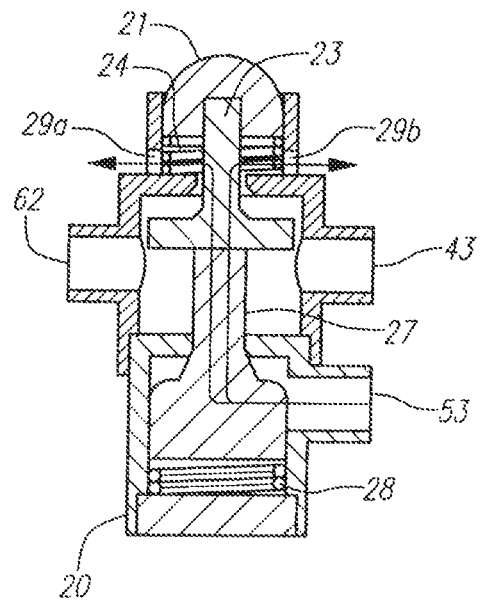
FIG. 4D illustrates the manifold of FIG. 3A manually released to relieve pressure in the device.

Tubular member 60 is connected to a delivery assembly comprising a manifold 20, check valve 22 and tubular members 41 and 51 extending from the manifold 20 for directing the delivery of the fluid 13 from the pressurized source 10 to one or more nasal catheters positioned in a patient's nasal cavity. As shown in FIGS. 4A-D, manifold 20 has an inlet channel 62 and two outlet channels 43 and 53. In use, inlet channel 62 is connected to tubular member 60 to receive fluid from the pressurized source. Outlet channel 53 is connected to tubular member 51 for delivering pressure and/or fluid 13 through a lumen of one or more nasal catheters to inflate a balloon on the distal end of the catheter(s). Outlet channel 43 is connected to tubular member 41 for delivering fluid 13 through a lumen of one or more nasal catheters and onto the surfaces of the nasal cavity. As shown in FIG. 4B, when the manifold 20 is pressurized, i.e., by liquid flowing through inlet 62 from the pressurized source 10, the liquid 13 pushes down on valve plug 27 to provide a path for allowing fluid 13 to flow thorough the manifold 20 and outlet channels 43 and 53 into tubular members 41 and 51. As shown in FIG. 4C, when the manifold 20 stops being pressurized, for example when the pressurized source 10 is removed or the valve thereon is closed, spring 28 is released causing the plug 27 to block passage of fluid and/or pressure from flowing in a distal, or reverse, direction from outlet channels 43 and 53. This allows an operator to exchange pressurized canisters, for example, if more cooling is desired, without deflating the balloons(s) on the distal end(s) of the nasal catheter(s). As shown in FIG. 4D, the manifold 20 also has a release button 21 connected to a pressure relief valve 23. Pressing down on the release button 21 pushes down on valve 23 and valve plug 27 to provide a passageway through vents 29a,b for pressure from outlet channels 43 and 53. The release button 21 enables the operator to release excess pressure to prevent a build up of pressure in the balloon(s) in fluid communication with outlet channel 51. In addition, by allowing pressure to flow distally from outlet channel 51 out relief vents 29a,b, the release button 21 may be used to control the amount of inflation of the balloon(s) and/or to deflate the balloon(s) once the treatment has been completed. In some embodiments, the pressure relief valve may alternatively be combined with the valve on the pressurized fluid container 10 so that there is one button for initiating cooling and one button for deflating the balloons at the completion of cooling.

As shown in FIGS. 1-2, tubular members 41 and 51 are connected to two multi-lumen nasal catheters 30a,b to deliver fluid from the pressurized source 10 to balloons 50a,b on the distal end of the catheters 30a,b and through ports 40a,b to a patient's nasal cavity. A check valve 22 in tubular member 41 prevents fluid from being delivered to the nasal catheter lumens connected to the delivery ports 40a,b on the nasal catheters 30a,b until the balloons 50a,b have been fully inflated to substantially occlude the nasal cavity. The check valve 22 remains closed until the pressure from the pressurized source 10 exceeds the balloon inflation pressure. Thus, the fluid initially flows through tubular member 51 and into the nasal catheter lumens connected to balloons 50a,b to inflate the balloons 50a,b. In some embodiments, fluid 13 from the pressurized fluid source 10 may flow through tubular member 60, manifold 20 and tubular member 51 into the nasal catheter lumens and balloons 50a,b. Once the fluid 13 enters the larger volume of the balloons 50a,b it will evaporate into the volume to inflate the balloon. Alternatively, as shown in FIG. 2, some embodiments may include a second pressure line 61 from the pressurized fluid source 10. The pressure line 61 is connected to the top of pressurized fluid container 10 so that it will be in fluid communication with the propellant or fluid vapor and not the liquid 13. Thus, the pressure line 61 can be used to deliver pressure to tubular member 51 to inflate the balloons 50a,b and tubular member 60 can be used to deliver fluid 13 through delivery ports 40a,b and to the patient's nasal cavity. Once the pressure exceeds the pressure required for balloon inflation, check valve 22 opens to allow fluid to flow through tubular member 41 and into the nasal catheter lumens connected to delivery ports 40a,b.

In some embodiments, as shown in FIGS. 1 and 2, the cooling assembly may comprise two multi-lumen nasal catheters 30a,b each having an expandable member 50a,b mounted on the distal end and a plurality of delivery ports 40a,b located in the distal region proximal to the balloons 50a,b for delivering the cooling fluid to each of a patients nostrils. Nasal catheters 30a,b have a length sufficient to extend through the patient's nasal cavity to the posterior nasal cavity or alternatively into the patient's nasopharynx. The plurality of delivery ports 40a,b are spaced apart longitudinally and axially along the outer walls of catheters 30a,b and distributed around the circumference of the catheter and spaced apart to cover the distance from about 3 cm to about 12 cm along the length of catheters 30a,b to deliver a liquid spray that substantially covers the surface of the patient's nasal cavity. Expandable members 50a,b, such as a flexible balloon are mounted circumferentially about the distal end of nasal catheters 30a,b are sized such that, upon expansion, they will fill the adjacent anatomy and create a seal.

In embodiments wherein the cooling assembly comprises two nasal catheters, as show in FIGS. 1-2, tubular member 51 may branch into two separate channels 52a,b for connecting to inflation lumens in each nasal catheter 30a,b. Likewise, tubular member 41 may branch into two separate channels 42a,b for connecting to fluid delivery lumens in each nasal catheter 30a,b. Check valve 22 is located before tubular member 41 branches into tubular members 42a,b. A connection manifold 25 connects channels 42a,b and 52a,b to the inflation and delivery lumens of each of the nasal catheters 30a,b. Alternatively, as shown in FIG. 1, the connection manifold 25 may connect channel 42a and 52a to delivery tube 32a and channels 42b and 52b to delivery tube 32a. Delivery tubes 32a and 32b can then be connected to nasal catheters 30a,b via a nasal manifold 26, which is designed to angle the nasal catheters 30a,b to provide patient comfort and better access to the nasal cavity. In other embodiments, the manifolds may be combined to simplify assembly and/or to reduce cost. For example, manifold 22 with splitter channels and pressure release valve 21 can be incorporated into the pressurized fluid source 10 so that there is one button to initiate cooling and another button to deflate the balloons for removal. Additionally or in the alternative, the connection manifold 25 can be incorporated into the nasal manifold 26.

Figure 9:
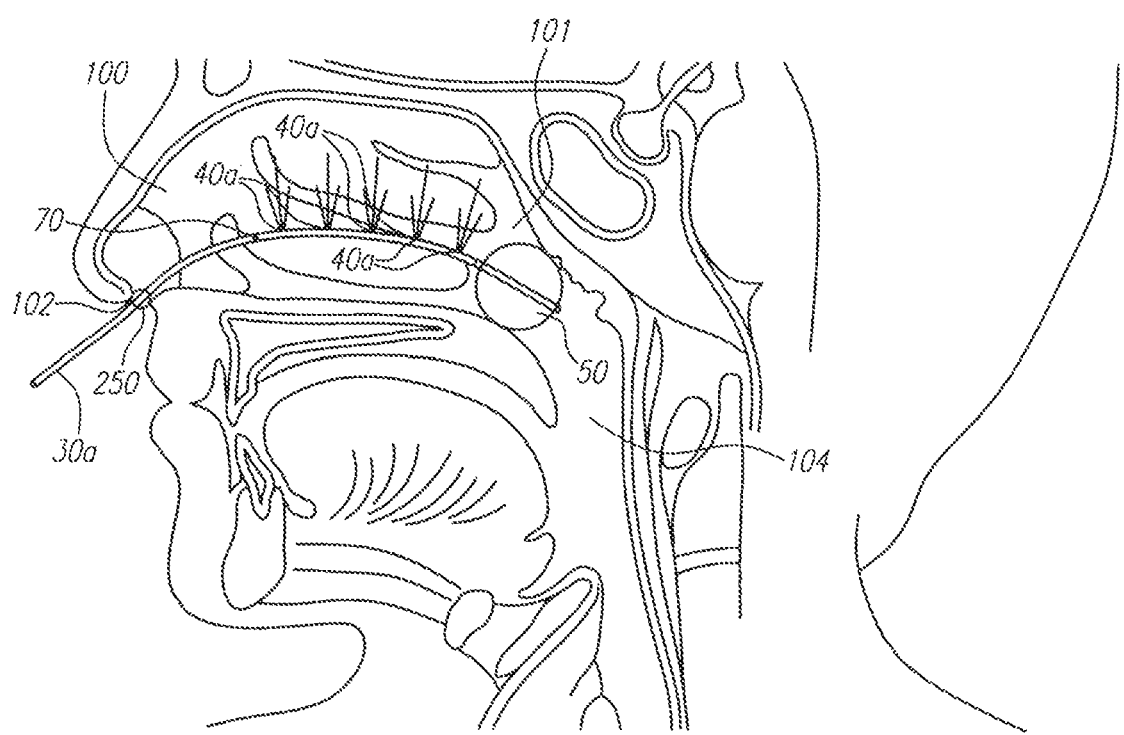
FIG. 9 illustrates an embodiment of a cooling assembly having a pressurized fluid source inserted into a patient's naval cavity for delivering a fluid to the nasal cavity for non-invasive cerebral and systemic cooling.

In use, as shown in FIG. 9 (illustrating use in one nostril), each of the dual catheters 30a,b of the cooling assembly are advanced into the patient's nostrils 102 such that balloons 50a,b are positioned in the posterior aspect of the patient's nasal cavity 101. In this embodiment, the balloons 50 may be positioned on either side of the nasal cavity before the septum. Fluid and/or pressure from the pressurized source 10 is delivered to the balloons 50a,b and the balloons 50a,b are inflated to conform to the posterior aspect of the nasal cavity 101 and form a seal isolating the nasal cavity 100 from the nasopharynx 104 and the rest of the patient's airways in order to prevent non-vaporized liquid 13 from leaking into the pharynx. Once isolated, a spray of liquid 13 may be delivered through delivery ports 40a,b into the patient's nasal cavity 101 and circulated though the nasal cavity 101 to allow for rapid cooling of the patient's head. The delivery ports 40a,b are designed to cause the liquid spray to spread in a pattern that will cover as much of the surface of the nasal cavity 101 as possible. In addition, the delivery ports 40a,b are designed to nebulize the liquid just prior to the liquid exiting the delivery ports 40a,b. Some of the fluid 13 though will evaporate during transit through the delivery system and become vapor. Thus, cooling will be provided by both the vapor, which is chilled from the evaporation that created it, the liquid spray as it evaporates in the nasal cavity. The volume of liquid delivered from a single pressurized canister may be range from about 0.05 to about 1 Liter. For example, it is envisioned that a single pressurized canister could deliver about 50 mL of cooling liquid, alternatively about 100 mL, alternatively about 200 mL, alternatively about 0.5 Liters, alternatively about 0.75 Liters, alternatively about 1 Liter of cooling liquid. Depending on the cooling fluid used, these volumes of cooling fluid may provide cooling for approximately 10 minutes, alternatively up to 30 minutes, alternatively up to one hour.

Figure 5:
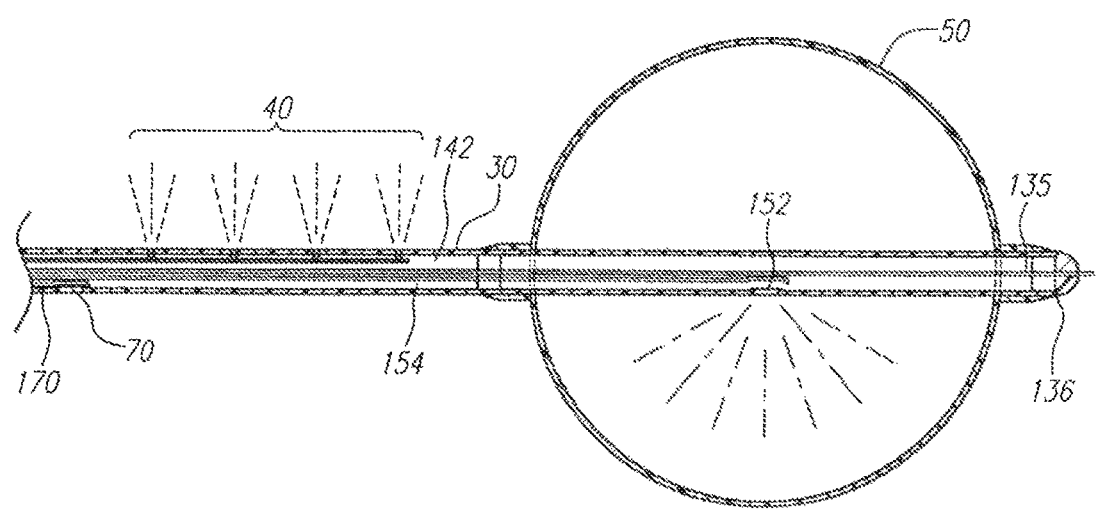
FIG. 5 illustrates an embodiment of the distal end of a nasal catheter tube for use with the cooling assembly for delivering a fluid to the nasal cavity for non-invasive cerebral and systemic cooling.
Figure 6:
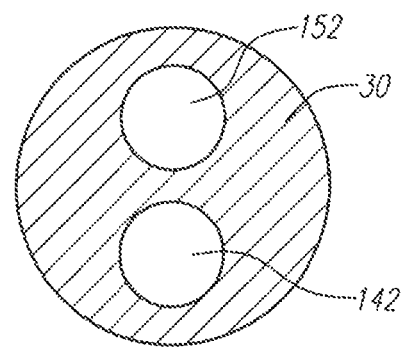
FIG. 6 illustrates a cross-section of an embodiment of the nasal catheter tube for use with the cooling assembly for delivering a fluid to the nasal cavity for non-invasive cerebral and systemic cooling.
Figure 7:
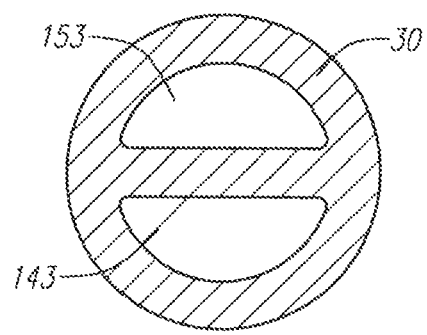
FIG. 7 illustrates a cross-section of an alternative embodiment of the nasal catheter tube for use with the cooling assembly for delivering a fluid to the nasal cavity for non-invasive cerebral and systemic cooling.
Figure 8:
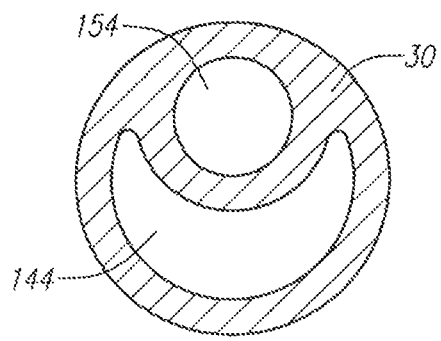
FIG. 8 illustrates a cross-section of an alternative embodiment of the nasal catheter tube for use with the cooling assembly for delivering a fluid to the nasal cavity for non-invasive cerebral and systemic cooling.

Any non-vaporized liquid may then be allowed to run out the patient's nostrils 102. In some embodiments, a second balloon 250 may be mounted on the catheter 30a proximal to the delivery ports to occlude the patient's nostril 102. In an alternative embodiment, as shown in FIG. 5, one or both of catheters 30a,b may further include a third lumen 170 in fluid communication with a suction port 70 proximal to the balloons 50a,b whereby the excess liquid may be suctioned from the patient's nasal cavity. In addition or alternatively, one or both nasal catheters 30a,b may include a third fourth lumen 135 extending between the distal and proximal ends of the catheter and having an opening at the distal and proximal ends and for providing a breathing passage through the nasal cavity while it is occluded by the balloons 50a,b.

Figure 10:
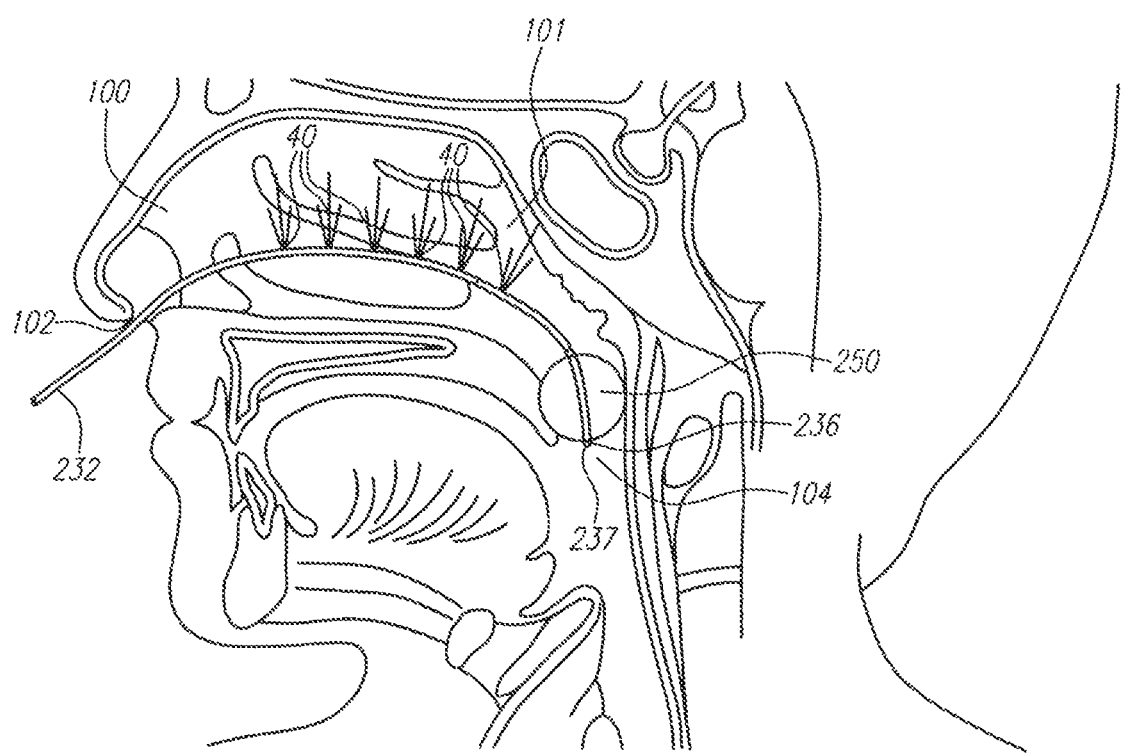
FIG. 10 illustrates an alternative embodiment of a cooling assembly having a pressurized fluid source inserted into a patient's naval cavity for delivering a fluid to the nasal cavity for non-invasive cerebral and systemic cooling.

In an alternative embodiment, as shown in FIG. 10, the cooling assembly comprises a single nasal catheter 232 having a balloon 250 mounted on the distal end and a plurality of ports 40a extending axially and longitudinally on the distal region is advanced into the patient's nostrils 102 until balloon 250 is positioned proximal to the nasopharynx 104. In this embodiment, the balloon 250 may be slightly larger than balloons 50a,b, or more compliant, such that when inflated balloon 250 will conform to the opening to the nasopharynx 104 to seal the nasal cavity 100 from the rest of the patient's airways and prevent non-vaporized liquid from leaking into the patient's throat and to prevent inhalation of the fluid vapors. Fluid and/or pressure from the pressurized source 10 is delivered to the balloon 250 and the balloon 250 is inflated to form a seal isolating the nasal cavity 100 from the nasopharynx 104. Once isolated, the spray of liquid 13 may be delivered through delivery ports 40 into the patient's nasal cavity 100 and circulated though the nasal cavity 100 to allow for rapid cooling of the patient's head. The non-vaporized liquid may then be allowed to run out the patient's other nostril. In an alternative embodiment, catheter 232 may further include a third lumen having a port proximal to the balloon 250 whereby the excess liquid may be suctioned from the patient's nasal cavity 100. In addition, catheter 232 may further include a third lumen extending between the distal and proximal ends of the catheter 232 and having an opening at the distal and proximal ends for providing a breathing passage through the nasal cavity while it is occluded by the balloon 250.

FIG. 5 illustrates one embodiment of a nasal catheter 30 having a balloon 50 mounted on the distal end and a plurality of delivery ports 40 extending longitudinally and axially in the distal region for non-invasive cerebral and systemic cooling of the nasal cavity. Nasal catheter 30 is operably sized to extend through the patient's nasal cavity. Nasal catheter 30 has at least two lumens 142 and 154 extending between proximal and distal ends of the catheters. Inflation lumen 154 is in fluid communication with balloon 50 for providing pressure and/or fluid from the pressurized fluid source to balloon 50 for inflating the balloon 50. Delivery lumen 142 is in fluid communication with a plurality of ports 40 located along the outer wall of catheter 30 for spraying the fluid into the nasal cavity. In use, delivery lumen 142 is connected to tubular member 41 for transporting the cooling fluid 13 from the pressurized fluid source through catheter 30 and delivery ports 40 into the patient's nasal cavity. These ports 40 are spaced apart longitudinally and axially along the outer walls of catheter 30. For example, there may be about 10-40 delivery ports distributed around the circumference of the catheter and spaced apart to cover the distance from about 3 cm to about 12 cm along the length of catheter 30. In use, when catheter 30 is placed in the nasal cavity of a patient, this distribution would provide full coverage of the nasal cavity. This distinction is critical in that dispersing the spray over a larger region permits greater cooling though evaporative heat loss. Furthermore, each of the plurality of delivery ports 40 will be designed so that the fluid flowing through the catheter lumen 142 will be nebulized just prior to entering the nasal cavity. In some embodiments, as shown in FIG. 5, catheter 30 may further include a third lumen 170 in fluid communication with a suction port 70 proximal to balloon 50 whereby the excess liquid may be suctioned from the patient's nasal cavity.

The ability to nebulize the liquid at each of the delivery ports 40 ensures that the distribution of varying sizes of liquid particles will be uniform throughout the nasal cavity. Specifically, when a liquid is nebulized, a spray with liquid particles of various sizes is created. If the liquid was nebulized at the proximal end of the nasal catheter or outside of the catheter and then transported as a nebulized liquid spray through the catheter lumen to the multiple delivery ports, the smaller liquid particles would flow through the proximal delivery ports while the larger liquid particles would be carried to the distal end of the tube before being delivered to the nasal cavity via one of the delivery ports near the distal end of the nasal catheter. This would result in an uneven distribution of the liquid particles within the nasal cavity. Conversely, when the liquid is transported through the nasal catheter and nebulized separately at each delivery port just prior to delivery, the size distribution of liquid particles distributed at any given point in the nasal cavity is uniform. This is critical because an even distribution of the varying sized liquid particles provides for better evaporation of the liquid spray, which results in better cooling through evaporative heat loss and is more tolerable to the patient The balloon 50 is fabricated of a fully compliant, elastomeric material such as blow molded polyurethane. In some embodiments, the balloon 50 may be configured to have maximum or fully inflated, diameter of about 10 mm, alternatively 15 mm, alternatively 20 mm, alternatively 25 mm, alternatively 35 mm depending upon the patient size and desired location for use of the balloon. For example, in some embodiments, the balloon 50 would be inserted into each nostril and inflated until it conforms to the choana (the paired openings between the nasal cavity and the nasopharynx) for creating a seal in the posterior naval cavity proximal to the nasal septum. Alternatively a single balloon may be advanced past the posterior nasal cavity and inflated diameter of about 25-35 mm to create a seal proximal to the patient's nasopharynx. The balloons may be adhesively bonded to the outside of the catheter shaft, or may be thermally bonded. Other suitable means of joining the balloons are also contemplated.

In some embodiments, as shown in FIG. 5, catheter 30 includes a third lumen 135 extending from proximal to distal ends of the catheter 30 and having proximal and distal openings such that lumen 135 provides a passage through the patient's nasal cavity while it is occluded by balloon 50. This third "breathing" lumen is in fluid communication with the patient's nasopharynx, pharynx, larynx, and/or esophagus, enabling the patient to breathe while the apparatus is inserted in the nasal cavity. Nasal catheter 30 also has rounded sealed tip 136 on the distal end, which seals the distal end of lumens 142 and 152 and provides a smooth surface to avoid damaging sensitive tissues.

FIGS. 6-8 illustrate alternative geometries for the delivery and inflation lumens of nasal catheter 30. The catheter shaft may be a unitary extruded multi-lumen tube which extends for the full length of the device, with the exception of the soft tip attached at the distal end. The multi-lumen tube is preferably formed of an extrudable polymer, such as Pebax, polyethylene, polyurethane, polypropylene, or nylon. The lumen shapes may be varied, for example, depending upon the cooling fluid used and the amount of evaporation expected during delivery of the fluid. For example, as shown in FIG. 6, in some embodiments, the cross-sections of delivery lumen 142 and inflation lumen 154 may be equal sized circular lumens. The circular lumens 142 and 154 have an advantage for being least kinkable design for a double lumen extrusion. Alternatively, as shown in FIG. 7, the cross-sections of delivery lumen 143 and inflation lumen 153 may be equal sized semi-circular lumens. The semi-circular lumens 142 and 153 will pass more gas/fluid so that for a given lumen area the semi-circular lumen extrusion can be smaller in diameter overall. Alternatively, as shown in FIG. 8, the cross-sections of delivery lumen 144 and inflation lumen 154 may be unequal sized crescent-shaped and circular lumens. Preferably the inflation lumen 154 will be smaller than the liquid delivery lumen 144. This extrusion with a crescent shape delivery lumen 144 also has the advantage of being able to make a wider range spray pattern for the delivery of the cooling fluid (if needed).

In an alternative embodiment, as shown in FIG. 3, the occlusion balloon 150 and cooling fluid delivery may be provided on separate nasal catheters 131, 132 inserted into both of the patient's nostrils. Here, a first nasal catheter 132 has a balloon 150 mounted on the distal end and a second nasal catheter 131 has a plurality of delivery ports 40 extending axially and longitudinally in the distal region. Nasal catheter 132 has at least one lumen connected to tubular member 51. In some embodiments, the distal end of nasal catheter 132 may extend distal of balloon 150 and a nasal catheter 132 may have a second lumen with an opening in the distal tip for providing the patient breathing access while balloon 150 is occluding the nasal cavity. Nasal Catheter 132 has a length sufficient to extend proximal to a patient's nasopharynx such that in use balloon 150 may be positioned proximal to the nasopharynx and be inflated to seal off the patient's nasal cavity from the patient's pharynx and airways. Nasal catheter 131 may be slightly shorter than nasal catheter 132 because nasal catheter 131 only needs to extend into patient's nasal cavity to deliver the cooling fluid through delivery ports 40. Nasal catheters 131, 132 may both be provided in a variety of lengths to accommodate the varying anatomy of patients, including pediatric and adult sizes. In use, nasal catheter 131 has at least one lumen connected to tubular member 41. As discussed previously, fluid 13 from the pressurized source 10 is first delivered through manifold 20 and tubular member 51 to nasal catheter 132 to inflate balloon 150. Once the pressure from the pressurized source 10 exceeds the balloon inflation pressure, check valve 22 opens and fluid 13 from the pressurized source 10 flows though manifold 20 and tubular member 41 to nasal catheter 131 and is delivered through ports 40 onto the surface of the patient's nasal cavity.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for cerebral cooling, the method comprising:

providing a cooling assembly including a first elongate tubular member having a proximal end, a distal end, a lumen extending therebetween, and a plurality of ports in fluid communication with the lumen, a second elongate tubular member having a proximal end, a distal end, a lumen extending therebetween, and a plurality of ports in fluid communication with the lumen, a manifold in fluid communication with the lumens of the first and the second elongate tubular members, the manifold further communicating with a third elongate tubular member, and a reservoir containing a pressurized fluid in communication with the third elongate tubular member, wherein the pressurized fluid includes a propellant having a boiling point less than 22° C.;

inserting the first elongate tubular member into a nasal cavity of a patient through a first nostril of the patient such that the plurality of ports are positioned in the nasal cavity;

inserting the second elongate tubular member into the nasal cavity through a second nostril of the patient such that the plurality of ports are positioned in the nasal cavity; and delivering the pressurized fluid onto a surface of the nasal cavity by infusing the pressurized fluid from the reservoir through the manifold, into the lumens and through the plurality of ports of the first and the second elongate tubular members;

wherein a check valve is situated between the manifold and the first and the second elongate tubular members, the check valve preventing the delivery of pressurized fluid onto the surface of the nasal cavity until a minimum inlet pressure of the pressurized fluid is obtained.

2. The method of claim 1, wherein the pressurized fluid further comprises a cooling fluid having a boiling point less than 37° C.

3. The method of claim 2, wherein the cooling fluid having a boiling point less than 37° C. is selected from the group consisting of a perfluorocarbon, a hydrofluorocarbon, and a fluorocarbon.

4. A method for cerebral cooling, the method comprising:
providing a cooling assembly including
a first elongate tubular member having a proximal end, a distal end, a lumen extending therebetween, and a plurality of ports in fluid communication with the lumen, a second elongate tubular member having a proximal end, a distal end, a lumen extending therebetween, and a plurality of ports in fluid communication with the lumen, a manifold in fluid communication with the lumens of the first and the second elongate tubular members, the manifold further communicating with a third elongate tubular member, and a reservoir containing a pressurized fluid in communication with the third elongate tubular member, wherein the pressurized fluid includes a propellant having a boiling point less than 22° C. and a cooling fluid having a boiling point less than 37° C.;

inserting the first elongate tubular member into a nasal cavity of a patient through a first nostril of the patient such that the plurality of ports are positioned in the nasal cavity;

inserting the second elongate tubular member into the nasal cavity through a second nostril of the patient such that the plurality of ports are positioned in the nasal cavity; and delivering the pressurized fluid onto a surface of the nasal cavity by infusing the pressurized fluid from the reservoir through the manifold, into the lumens and through the plurality of ports of the first and the second elongate tubular members;

wherein a check valve is situated between the manifold and the first and the second elongate tubular members, the check valve preventing the delivery of pressurized fluid onto the surface of the nasal cavity until a minimum inlet pressure of the pressurized fluid is obtained.

* * * * *